United States Patent
Haussmann et al.

(10) Patent No.: US 6,531,632 B2
(45) Date of Patent: Mar. 11, 2003

(54) BIS-O-AMINOPHENOLS AND O-AMINOPHENOLCARBOXYLIC ACIDS AND PROCESS FOR PREPARING THE SAME

(75) Inventors: Jörg Haussmann, Erlangen (DE); Gerhard Maier, München (DE); Recai Sezi, Röttenbach (DE)

(73) Assignee: Infineon Technologies AG, Munich (DE)

( * ) Notice: Subject to any disclaimer, the term of this patent is extended or adjusted under 35 U.S.C. 154(b) by 67 days.

(21) Appl. No.: 09/803,762

(22) Filed: Mar. 12, 2001

(65) Prior Publication Data

US 2002/0010370 A1 Jan. 24, 2002

(Under 37 CFR 1.47)

(30) Foreign Application Priority Data

Mar. 10, 2000 (DE) .......................................... 100 11 608

(51) Int. Cl.$^7$ .............................................. C07C 211/43
(52) U.S. Cl. ...................... 564/427; 564/426; 546/81; 546/88; 562/452
(58) Field of Search ................ 564/426, 427; 546/81, 88; 562/452

(56) References Cited

FOREIGN PATENT DOCUMENTS

| | | |
|---|---|---|
| EP | 0 905 123 A1 | 3/1999 |
| EP | 0 905 124 A1 | 3/1999 |
| EP | 0 906 903 A2 | 4/1999 |
| EP | 0 918 050 A1 | 5/1999 |

*Primary Examiner*—Samuel Barts
(74) *Attorney, Agent, or Firm*—Laurence A. Greenberg; Werner H. Stemer; Ralph E. Locher

(57) ABSTRACT

Bis-o-aminophenols and o-aminophenolcarboxylic acids have the following structures:

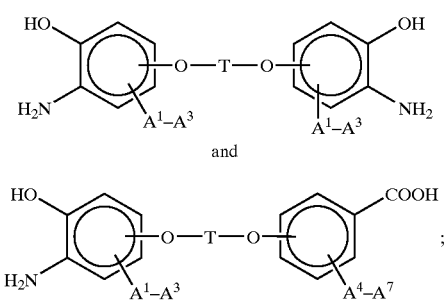

and $A^1$ to $A^7$ are, independently of each other, H, F, $CH_3$, $CF_3$, $OCH_3$ or $OCF_3$. T is an aromatic or heterocyclic residue. A method for preparing bis-o-aminophenols and o-aminophenolcarboxylic acids is also provided.

16 Claims, No Drawings

BIS-O-AMINOPHENOLS AND O-AMINOPHENOLCARBOXYLIC ACIDS AND PROCESS FOR PREPARING THE SAME

BACKGROUND OF THE INVENTION

FIELD OF THE INVENTION

The invention relates to novel bis-o-aminophenols and o-aminophenolcarboxylic acids and to a method for their preparation.

Bis-o-aminophenols and o-aminophenolcarboxylic acids are needed in particular for the preparation of high-temperature-stable polymers such as polybenzoxazoles (PBO) and intermediates for their preparation, and for the preparation of hydroxypolyimides (see, for example, European Patent EP 0 264 678 and European Patent EP 0 300 326). PBO intermediates can be prepared in a way such that a dicarboxylic acid chloride is reacted with a bis-o-aminophenol. Whereas, however, numerous dicarboxylic acids and their acid chlorides are available as a result of the diversity of their industrial uses, there are comparatively few bis-o-aminophenols. Moreover, the kind of aminophenol used exerts a considerable influence on the spectrum of properties of the polymer prepared from it. Thus not only the thermal, electrical and mechanical behavior, but also the solubility, stability towards hydrolysis and many other characteristics of the polymer are strongly influenced by the aminophenol used in the preparation.

PBO intermediates can be structured directly at reasonable cost in the form of a photosensitive compound, i.e. without an auxiliary resist. In comparison with other directly photostructurable dielectrics such as polyimide (PI) and benzocyclobutene (BCB), PBO intermediates have the advantage of positive structurability and aqueous alkaline development (see European Patent EP 0 023 662 and European Patent EP 0 264 678). For this purpose the PBO intermediates used must be largely transparent at the exposure wavelength and sufficiently soluble in—preferably metal ion-free—developers. As is the case for the polyimides, polybenzoxazoles also have the great advantage that—in comparison with the cyclized final products—they can be applied to the substrate as readily soluble intermediates and then cyclized on the substrate itself, whereby the solubility and therefore the sensitivity towards solvents and other process chemicals strongly decreases.

Good electrical, mechanical and thermal characteristics are necessary for the use of polybenzoxazoles in microelectronics, in particular as a dielectric between two metal layers, e.g. in multi-chip modules and memory and logic chips, or as a buffer coat between the chip and its outline. When using polymers of the above kind as a dielectric between metallic printed conductors it is very important that the metal not diffuse through the dielectric at high temperature, i.e. at temperatures greater than 300° C. But many metals, especially aluminum, which is currently the most commonly used metal, do diffuse through the dielectric at high temperatures. For this reason the metal is coated with a barrier layer, for example of titanium nitride or a combination of titanium and titanium nitride, which prevents the diffusion of the metal into the dielectric. The use of an additional layer, however, adds significantly to the costs and also requires more time.

Up to now there has been a lack of suitable bis-o-aminophenols and o-aminophenolcarboxylic acids for the preparation of polymers able to meet the strongly increased requirements of the microelectronics sector. Comparable monomers are known, for example, from European Patent Application EP 0 110 420, European Patent Application EP 0 317 942, European Patent Application EP 0 905 123 and European Patent Application EP 0 906 903. But there is no information on the diffusion of metals in the polymers prepared from these after cylization on a substrate (see: European Patent EP 0 264 678 and European Patent Application EP 0 317 942).

SUMMARY OF THE INVENTION

It is accordingly an object of the invention to provide bis-o-aminophenols and o-aminophenolcarboxylic acids and a method for preparing the same, which overcome the hereinafore-mentioned disadvantages of the heretofore-known compounds and methods of this general type and which are suitable for the preparation of polymers that meet the strongly increased requirements of microelectronics. In particular, these monomers are intended to enable the preparation of readily soluble polymer intermediates which after cyclization on a substrate produce polybenzoxazoles with high temperature stability and, above all, with significantly reduced metal diffusion.

With the foregoing and other objects in view there is provided, in accordance with the invention, bis-o-aminophenols and o-aminophenolcarboxylic acids having structures represented by the respective formulas:

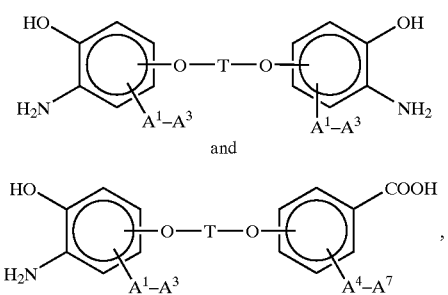

wherein
  each of $A^1$ to $A^7$ is a univalent ring substituent independently selected from the group consisting of H, F, $CH_3$, $CF_3$, $OCH_3$ and $OCF_3$;
  T is a bivalent polycyclic linking member selected from the group consisting of

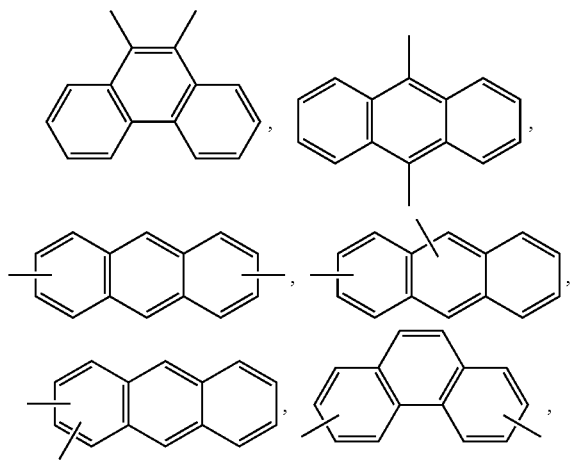

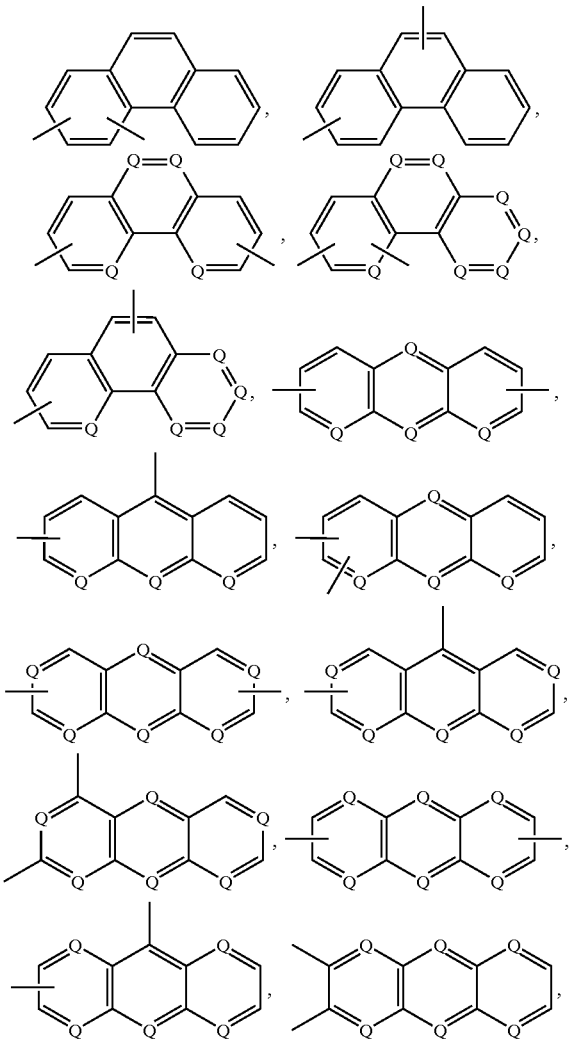

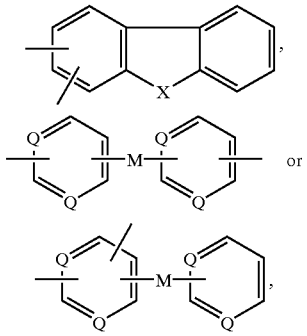

wherein independently at each occurrence Q is selected from the group consisting of C—H, C—F, C—CH$_3$, C—CF$_3$, C—OCH$_3$, C—OCF$_3$ or N, provided that at least one Q signifies N and a maximum of two N atoms may be present in a single ring,

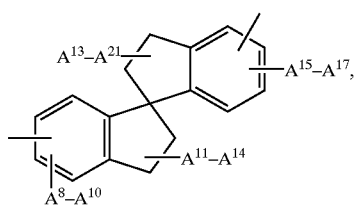

wherein each of A$^8$ to A$^{21}$ is a univalent ring substituent independently selected from the group consisting of H, F, CH$_3$, CF$_3$, OCH$_3$ and OCF$_3$;

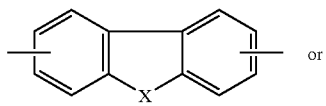

wherein X signifies CH$_2$, CF$_2$, C(CH$_3$)$_2$, C(CF$_3$)$_2$, C(OCH$_3$)$_2$, C(OCF$_3$)$_2$, C(CH$_3$) (C$_6$H$_5$), C(C$_6$H$_5$)$_2$, O, N—H, N—CH$_3$ or N—C$_6$H$_5$;

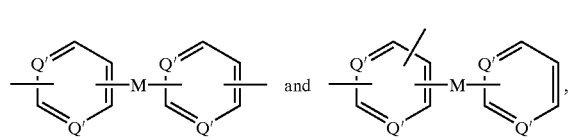

wherein
independently at each occurrence Q' is selected from the group consisting of C—H, C—F, C—CH$_3$, C—CF$_3$, C—OCH$_3$, C—OCF$_3$ or N,
and M is a bivalent linking member selected from the group consisting of

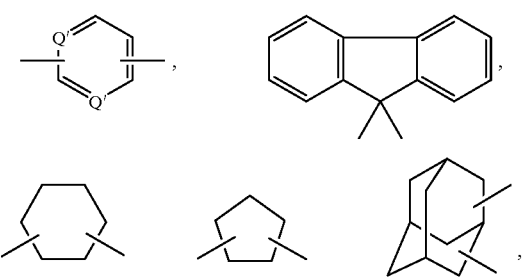

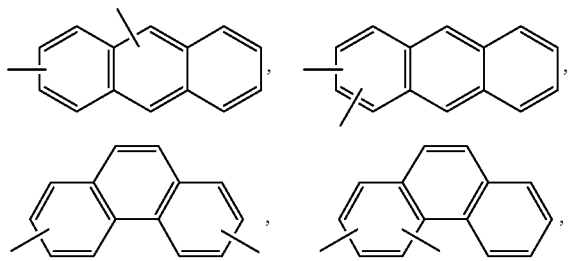

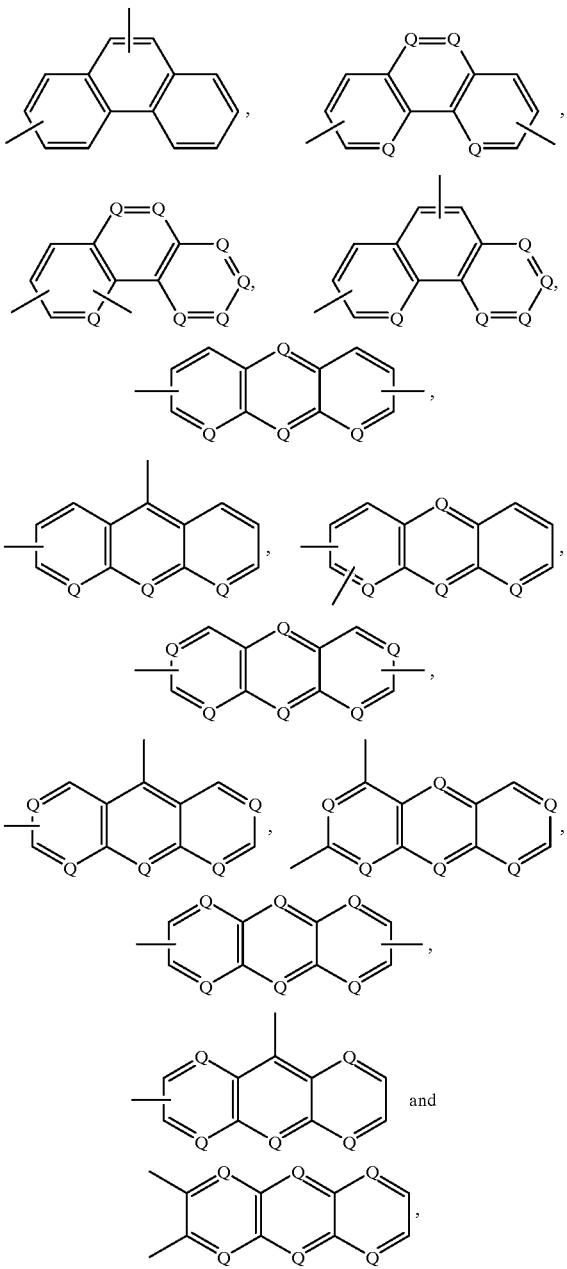

wherein Q and Q' are as defined above.

The designations "$A^1$–$A^3$", "$A^4$–$A^7$", "$A^8$–$A^{10}$", "$A^{11}$–$A^{14}$", "$A_{15}$–$A^{17}$" and "$A^{18}$–$A^{21}$" in the structural formulae mean that the phenyl groups or cyclic structures carry respectively the residues $A^1$, $A^2$ and $A^3$, or $A^4$, $A^5$, $A^6$ and $A^7$, or $A^8$, $A^9$ and $A^{10}$, or $A^{11}$, $A^{12}$, $A^{13}$ and $A^{14}$, or $A^{15}$, $A^{16}$ and $A^{17}$, or $A^{18}$, $A^{19}$, $A^{20}$ and $A^{21}$.

With the objects of zhe invention in view, there are also provided novel o-nitrophenyl ether compounds from which the bis(o-aminophenols) and o-aminophenolcarboxylic acids of the invention can be prepared by a sequence of reactions as detailed below. The o-nitrophenyl ether compounds of the invention are represented by the formula

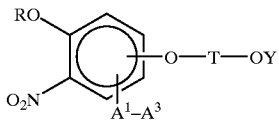

wherein $A^1$–$A^3$ and T are defined as above, R is a residue selected from the group consisting of alkyl, alkoxyalkyl, alkenyl, alkoxyalkenyl, alkynyl and alkoxyalkynyl residues with a maximum of 6 C atoms in each case, and phenyl, phenacyl $C_6H_5CO$—$CH_2$—, benzyl, benzylalkyl, benzylalkenyl, benzyloxyalkyl, benzyloxyalkenyl, benzylalkoxyalkyl and benzylalkoxyalkenyl residues with a maximum of 4 aliphatic C atoms in each, case, and Y is selected from the group consisting of

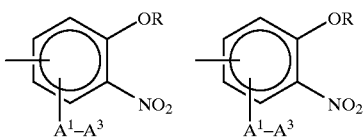

and H.

The bis(o-aminophenols) and o-aminophenolcarboxylic acids of the invention are advantageously prepared by a simple synthesis utilizing novel o-nitrophenyl ether compounds of the invention as starting materials, that can be carried out with high reproducibility. Compared to known bis-o-aminophenols and o-aminophenolcarboxylic acids having different T groups, the reactivity of the compounds of the invention with a carboxylic acid derivative such as an acid chloride is unexpectedly modulated so as to increase the selectivity of reaction at the amino group and thus favoring the conversion of the compounds of the invention to polymer intermediates in high yield and purity.

In these novel compounds, the special structure is clearly responsible for the unexpectedly good barrier effect which the polymer intermediates prepared from them exert against metal diffusion. Dielectrics prepared from these kinds of polybenzoxazole intermediates show in particular a significant reduction in aluminum diffusion. This removes the need for an additional barrier layer.

With the objects of the invention in view, there is also provided a process for preparing the respective bis(o-aminophenols) and o-aminophenolcarboxylic acids.

The method used to prepare the bis-o-aminophenols and o-aminophenolcarboxylic acids begins with the reaction of a dihydroxy compound represented by the formula

HO—T—OH,

T being defined as above, with a halogenated o-nitrophenol ether derivative represented by the formula (2)

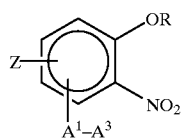

in which Z is a halogen atom, preferably fluorine, and R and $A^1$–$A^3$ are defined above.

The reaction takes place in a solvent at a temperature of 50 to 150° C. in the resence of a base.

In the preparation of bis-o-aminophenols the reactants HO—T—OH (1) and (2) are used in the molar ratio of approximately 1:2, whereby the reaction proceeds in the following way:

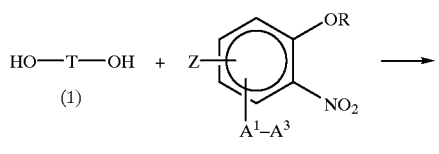

(1)    (2)

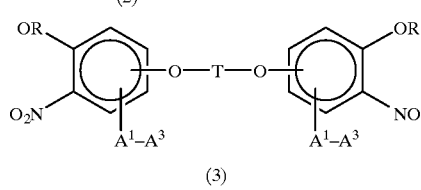

(3)

In the preparation of o-aminophenolcarboxylic acids the reactants (1) and (2) are used in an approximately equimolar ratio whereby the reaction proceeds as follows:

HO—T—OH + (2) →

(1)

(4)

The novel reaction product (4) is then treated with a halogenated benzoic acid ester (5) in a solvent at a temperature of 50 to 150° C. in the presence of a base. The following reaction takes place:

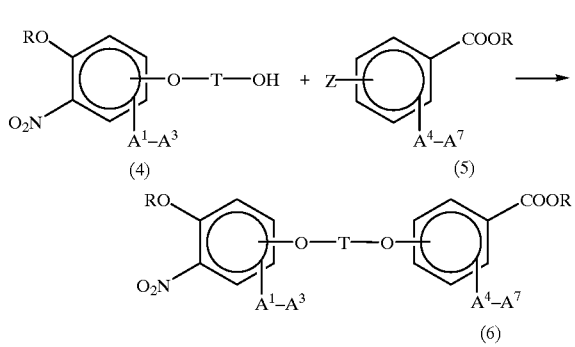

(4)    (5)

(6)

The novel nitrophenyl ether reaction products (3) and (6) are then subjected to reduction and cleavage and reaction product (6) is also subjected to hydrolysis. The following reactions take place with the formation of the bis-o-aminophenols (7) and o-aminophenolcarboxylic acids (8) according to the invention:

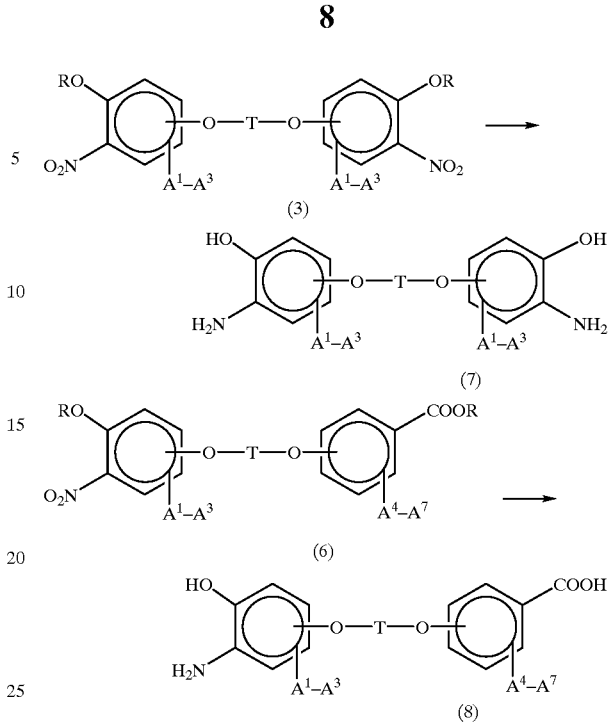

(3)

(7)

(6)

(8)

The reduction of the nitro compounds (3) and (6) can, for example, be carried out by hydrogenation with hydrogen on palladium/active charcoal (Pd/C). In principle, however, any method which can be used for reducing a nitro group to an amino group is suitable.

Removal of the R group in the compounds (3) and (6) can be carried out using, for example, trifluoroacetic acid or titanium tetrachloride. The hydrolysis of the ester group in the compounds (6) can be carried out using, for example, potassium hydroxide.

Reduction and cleavage, or reduction, cleavage and hydrolysis can be performed in separate steps; these steps can be carried out in any order. It is advantageous, however, to perform these reactions, i.e. reduction and cleavage, or reduction, cleavage and hydrolysis, simultaneously, i.e. together. This is preferably performed through hydrogenation with hydrogen on Pd/C.

The base is preferably a carbonate or bicarbonate of an alkali metal or alkaline earth metal, such as sodium carbonate ($Na_2CO_3$) or potassium carbonate ($K_2CO_3$). It can also be advantageous to use an organic base with a tertiary nitrogen atom, for example triethylamine, tetramethylethylenediamine, N-ethylmorpholine, quinoline or pyridine.

The polymer intermediates prepared from the bis-o-aminophenols and o-aminophenolcarboxylic acids according to the invention are readily soluble in many organic solvents such as acetone, ethyl lactate, N-methylpyrrolidone, diethylene glycol mono- or diethyl ether, cyclohexanone and γ-butyrolactone, and also in aqueous alkaline developers containing no metal ions. They are therefore well suited as base polymers for positive photo-structurable dielectrics which can be developed with aqueous alkali. Using the centrifugal technique the intermediates can be easily applied to the substrate, such as a silicon wafer; they form even films and can be readily cyclized on the substrate. A particular advantage of the intermediates prepared from bis-o-aminophenols and o-aminophenolcarboxylic acids in comparison with intermediates of prior art is significantly reduced metal diffusion.

Other features which are considered as characteristic for the invention are set forth in the appended claims.

Although the invention is illustrated and described herein as embodied in novel bis(o-aminophenols), o-aminophenolcarboxylic acids and o-nitrophenyl ether compounds and a process for preparing the same, it is nevertheless not intended to be limited to the details given, since various modifications and structural changes may be made therein without departing from the spirit of the invention and within the scope and range of equivalents of the claims.

The structure and method of preparation of the invention, however, together with additional objects and advantages thereof will be best understood from the following description of specific embodiments when read in connection with the following examples.

EXAMPLE 1

Preparation of 9,9-bis(4-[(3-benzyloxy-4-nitro)phenoxy]phenyl)fluorene

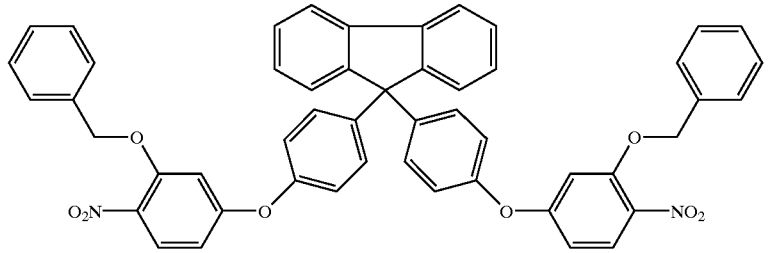

100.0 g of 9,9-bis(4-hydroxyphenyl)fluorene (0.285 mol) and 142.5 g of 3-fluoro-6-nitrobenzyloxybenzene (0.576 mol) are dissolved in 1050 ml of dimethylformamide. 200.0 g of $K_2CO_3$ (1.447 mol) is then added and the mixture stirred continuously for 3 hours at 135° C. At the end of the reaction the mixture is cooled to room temperature and poured with stirring into 2.5 l of ice water. The yellow solid which precipitates is filtered off using a Büchner funnel, washed once with dilute acetic acid and once with water and then dried in a vacuum chamber under nitrogen at 50° C./50 mbar.

For purification the crude product is dissolved in 800 ml of tetrahydrofuran at the boiling point and 800 ml of petroleum ether (bp 60–80° C.) is added. For crystallization the solution is kept at 4° C. for 12 hours and the white solid filtered off using a Büchner funnel and dried in the vacuum cabinet under nitrogen at 50° C./50 mbar. Yield: 211.0 g.

Characterization

Mass spectrum: molecular ion at 804

Elemental analysis:

|  | C | H | N |
| --- | --- | --- | --- |
| Required (%): | 76.1 | 4.5 | 3.5 |
| Found (%): | 76.1 | 4.4 | 3.5 |

EXAMPLE 2

Preparation of 9,9-bis(4-[(4-amino-3-hydroxy)phenoxy]phenyl)fluorene

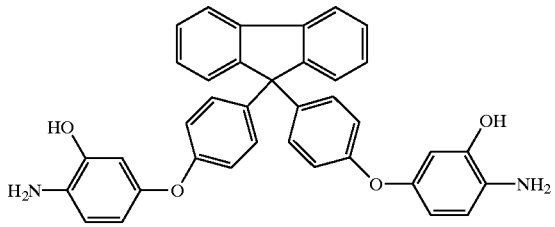

70.0 g of 9,9-bis(4-[(3-benzyloxy-4-nitro)phenoxy]phenyl)fluorene (0.087 mol) prepared according to Example 1 is dissolved in 700 ml of tetrahydrofuran, 7.0 g of palladium on active charcoal is added to the solution and the suspension is hydrogenated at room temperature in an autoclave with hydrogen at a pressure of 2 bar; the reaction is complete after 24 hours. The suspension is then filtered through a Buchner funnel and the red filtrate is evaporated to dryness in a rotary evaporator.

For purification the orange colored crude product is dissolved in 500 ml of tetrahydrofuran at the boiling point and 150 ml of petroleum ether (bp 60–80° C.) is added. For crystallization the solution is kept at 4° C. for 12 hours and the pale yellow solid filtered off using a 2uchner funnel and dried in the vacuum cabinet under nitrogen at 50° C./50 mbar. Yield: 47.2 g.

Characterization

Mass spectrum: molecular ion at 564

Elemental analysis:

|  | C | H | N |
| --- | --- | --- | --- |
| Required (%): | 78.7 | 5.0 | 5.0 |
| Found (%): | 78.6 | 5.1 | 3.5 |

EXAMPLE 3

Preparation of 9-(4-[(3-benzyloxy-4-nitro)phenoxy]phenyl)-9-(4-hydroxyphenyl)fluorene

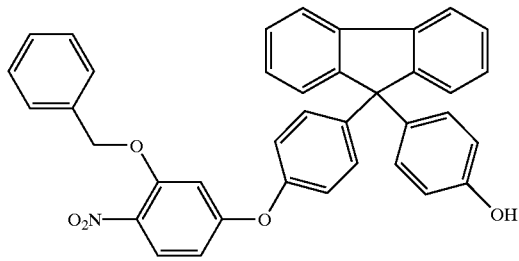

50.0 g of 9,9-bis(4-hydroxyphenyl)fluorene (0.143 mol) and 35.28 g of 3-fluoro-6-nitrobenzyloxybenzene (0.143 mol) are dissolved in 550 ml of dimethylformamide. 100.0 g of $K_2CO_3$ (0.724 mol) is then added and the mixture is stirred at 120° C. for 5 hours. At the end of the reaction the mixture is cooled to room temperature and poured with stirring into 1.0 l of ice water. The yellow solid which precipitates is filtered off using a Büchner funnel, washed once with dilute acetic acid and once with water and then dried in a vacuum chamber under nitrogen at 50° C./50 mbar.

The crude product is purified by recrystallization according to Example 1 with 350 ml of tetrahydrofuran and 350 ml of petroleum ether. Yield: 73.51 g.

Characterization

Mass spectrum: molecular ion at 577

Elemental analysis:

|  | C | H | N |
| --- | --- | --- | --- |
| Required (%): | 79.0 | 4.7 | 2.4 |
| Found (%): | 78.8 | 4.7 | 2.4 |

EXAMPLE 4

Preparation of 9-(4-[(3-benzyloxy-4-nitro)phenoxy]phenyl)-9-(4-[(2-trifluoromethyl-4-benzylcarboxy)phenoxy]phenyl)fluorene

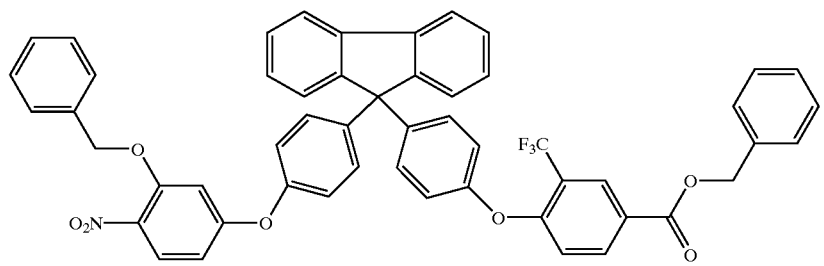

50.0 g of 9-(4-[(3-benzyloxy-4-nitro)phenoxy]phenyl)-9-(4-hydroxyphenyl)fluorene (0.0866 mol) prepared according to Example 3 and 25.83 g of 4-fluoro-3-trifluoromethylbenzoic acid benzyl ester (0.0866 mol) are dissolved in 400 ml of dimethylformamide. 31.40 g of $K_2CO_3$ (0.2272 mol) is then added and the mixture is stirred for 3 hours at 135° C. At the end of the reaction the mixture is cooled to room temperature, filtered through a fluted filter paper and poured into 1 l of water. It is then extracted 3 times with a total of 600 ml of ethyl acetate. The combined organic phases are washed twice more with water and the colorless solution obtained is evaporated to dryness in a rotary evaporator to yield a white solid.

The crude product is purified by recrystallization according to Example 1 with 350 ml of tetrahydrofuran and 350 ml of petroleum ether. Yield: 68.64 g.

Characterization

Mass spectrum: molecular ion at 855

Elemental analysis:

|  | C | H | N |
| --- | --- | --- | --- |
| Required (%): | 74.4 | 4.2 | 1.6 |
| Found (%): | 74.5 | 4.2 | 1.6 |

EXAMPLE 5

Preparation of 9-(4-[(4-amino-3-hydroxy)phenoxy)phenyl)-9-(4-[2-trifluoromethyl-4-carboxy]phenoxy)phenyl)fluorene

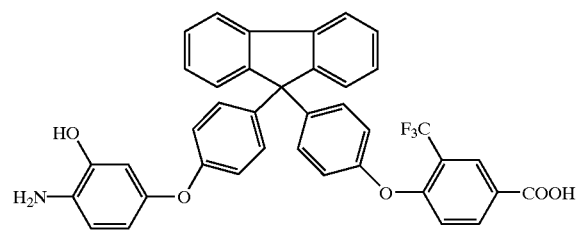

50.0 g of 9-(4-[(3-benzyloxy-4-nitro)phenoxy]phenyl)-9-(4-[(2-trifluoromethyl-4-benzylcarboxy)phenoxy]phenyl)fluorene (0.058 mol) prepared according to Example 4 is dissolved in 700 ml of tetrahydrofuran, 5.0 g of palladium on active charcoal is added to the solution and the suspension is hydrogenated at room temperature in an autoclave with hydrogen at a pressure of 2 bar; the reaction is complete after 24 hours. The suspension is then filtered through a Büchner funnel and the pale brown filtrate is evaporated to dryness in a rotary evaporator.

The crude product is purified by recrystallization according to Example 2 with 350 ml of tetrahydrofuran and 100 ml of petroleum ether. Yield: 35.2 g.
Characterization
Mass spectrum: molecular ion at 645
Elemental analysis:

|               | C    | H   | N   |
|---------------|------|-----|-----|
| Required (%): | 72.6 | 4.1 | 2.2 |
| Found (%):    | 72.7 | 4.1 | 2.1 |

EXAMPLE 6

Preparation of 4,7-bis[(3-benzyloxy-4-nitro) phenoxy]-1,10-phenanthroline

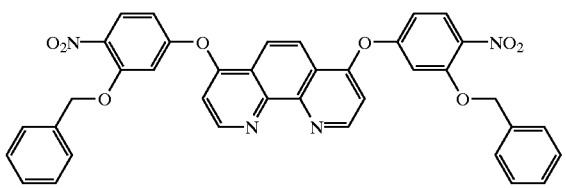

25.0 g of 4,7-dihydroxy-1,10-phenanthroline (0.118 mol) and 59.8 g of 3-fluoro-6-nitrobenzyloxybenzene (0.241 mol) are dissolved in 250 ml of dimethyl sulfoxide. 40.8 g of K$_2$CO$_3$ (0.295 mol) is then added and the mixture is stirred at 120° C. for 6 hours. At the end of the reaction the mixture is cooled to room temperature and poured with stirring into 700 ml of water. The yellow solid which precipitates is filtered off using a Buchner funnel, washed once with dilute acetic acid and once with water and then dried in a vacuum chamber under nitrogen at 50° C./50 mbar.

The crude product is purified by recrystallization according to Example 1 with 300 ml of tetrahydrofuran and 300 ml of petroleum ether. Yield: 68.0 g.
Characterization
Mass spectrum: molecular ion at 666
Elemental analysis:

|               | C    | H   | N   |
|---------------|------|-----|-----|
| Required (%): | 68.5 | 3.9 | 8.4 |
| Found (%):    | 68.3 | 3.9 | 8.4 |

EXAMPLE 7

Preparation of 4,7-bis[(4-amino-3-hydroxy) phenoxy]-1,10-phenanthroline

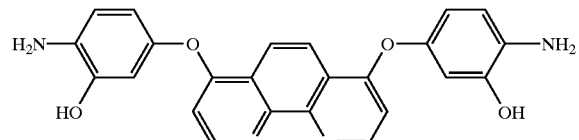

50 g of 4,7-bis[(3-benzyloxy-4-nitro)phenoxy]-1,10-phenanthroline (0.075 mol) prepared according to Example 6 is dissolved in 700 ml of tetrahydrofuran, 5.0 g of palladium on active charcoal is added to the solution and the suspension is hydrogenated at room temperature in an autoclave with hydrogen at a pressure of 2 bar; the reaction is complete after 24 hours. The suspension is then filtered through a Büachner funnel and the reddish brown filtrate is evaporated to dryness in a rotary evaporator.

The crude product is purified by recrystallization from ethyl acetate and petroleum ether (bp 60–80° C.) and the pale brown solid dried in a vacuum chamber under nitrogen at 50° C./50 mbar. Yield: 29.8 g.
Characterization
Mass spectrum: molecular ion at 426
Elemental analysis:

|               | C    | H   | N    |
|---------------|------|-----|------|
| Required (%): | 67.6 | 4.3 | 13.1 |
| Found (%):    | 67.6 | 4.4 | 13.0 |

EXAMPLE 8

Preparation of 4-[(3-benzyloxy-4-nitro) phenoxy]-7-hydroxy-1,10-phenanthroline

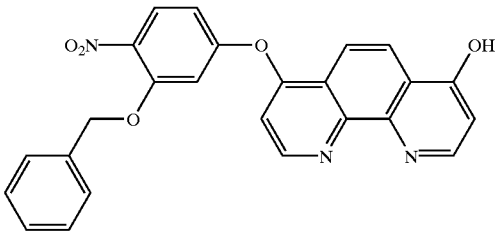

25.0 g of 4,7-dihydroxy-1,10-phenanthroline (0.118 mol) and 29.2 g of 3-fluoro-6-nitrobenzyloxybenzene (0.118 mol) are dissolved in 500 ml of dimethyl sulfoxide. 40.8 g of K$_2$CO$_3$ (0.295 mol) is then added and the mixture stirred continuously for 12 hours at 110° C. At the end of the reaction the mixture is cooled to room temperature and poured with stirring into 700 ml of water. The precipitated solid is filtered off using a Büchner funnel, washed once with dilute acetic acid and once with water and then dried in a vacuum chamber under nitrogen at 50° C./50 mbar.

The crude product is purified by recrystallization according to Example 1 with 200 ml of tetrahydrofuran and 200 ml of petroleum ether. Yield: 45.3 g
Characterization
Mass spectrum: molecular ion at 439
Elemental analysis:

|               | C    | H   | N   |
|---------------|------|-----|-----|
| Required (%): | 68.3 | 3.9 | 9.6 |
| Found (%):    | 68.3 | 3.9 | 9.6 |

EXAMPLE 9

Preparation of 4-[(3-benzyloxy-4-nitro)phenoxy]-7-[(4-benzylcarboxy)phenoxy]-1,10-phenanthroline

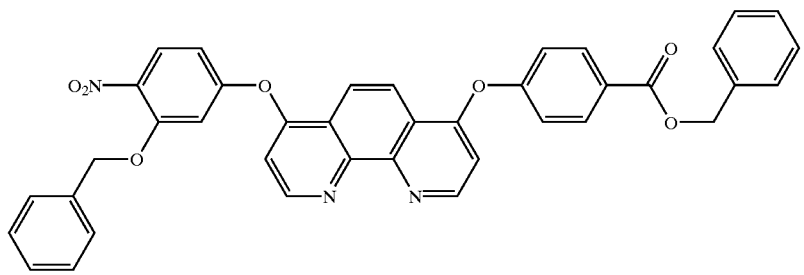

25.0 g of 4-[(3-benzyloxy-4-nitro)phenoxy]-7-hydroxy-1,10-phenanthroline (0.057 mol) prepared according to Example 8 and 13.1 g of 4-fluorobenzoic acid benzyl ester (0.057 mol) are dissolved in 500 ml of dimethyl sulfoxide. 40.8 g of $K_2CO_3$ (0.295 mol) is then added and the mixture is stirred for 8 hours at 135° C. At the end of the reaction the mixture is cooled to room temperature, filtered through a fluted filter paper and poured into 700 ml of water. It is then extracted 3 times with a total of 600 ml of ethyl acetate. The combined organic phases are washed twice more with water and the colorless solution obtained is evaporated to dryness in a rotary evaporator to yield a white solid.

The crude product is purified by recrystallization according to Example 1 with 200 ml of tetrahydrofuran and 200 ml of petroleum ether. Yield: 35.7 g Characterization Mass spectrum: molecular ion at 649

Elemental analysis:

|  | C | H | N |
|---|---|---|---|
| Required (%): | 72.1 | 4.2 | 6.5 |
| Found (%): | 72.1 | 4.3 | 6.6 |

EXAMPLE 10

Preparation of 4-[(4-amino-3-hydroxy)phenoxy]-7-[(4-carboxy)phenoxy]-1-10-phenanthroline

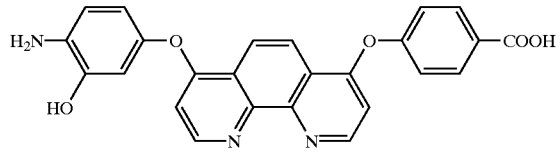

25.0 g of 4-[(3-benzyloxy-4-nitro)phenoxy]-7-[(4-benzylcarboxy)phenoxy]-1,10-phenanthroline (0.038 mol) prepared according to Example 9 is dissolved in 400 ml of tetrahydrofuran, 2.5 g of palladium on active charcoal is added to the solution and the suspension is hydrogenated at room temperature in an autoclave with hydrogen at a pressure of 2 bar; the reaction is complete after 24 hours. The suspension is then filtered through a Büchner funnel and the pale brown filtrate is evaporated to dryness in a rotary evaporator.

For purification the crude product is dissolved in 200 ml of tetrahydrofuran at the boiling point and 250 ml of petroleum ether (bp 60–80° C.) is added. For crystallization the solution is kept at 4° C. for 24 hours and the pale brownish solid filtered off using a Büchner funnel and dried in the vacuum cabinet under nitrogen at 50° C./50 mbar. Yield: 15.5 g.

Characterization

Mass spectrum: molecular ion at 439

Elemental analysis:

|  | C | H | N |
|---|---|---|---|
| Required (%): | 68.3 | 3.9 | 9.6 |
| Found (%): | 68.2 | 4.0 | 9.6 |

EXAMPLE 11

Preparation of 6,6'-bis[(3-benzyloxy-4-nitro)phenoxy]-5,5'-dimethyl-3,3,3',3'-tetramethyl-1,1'-spiro-bis(indane)

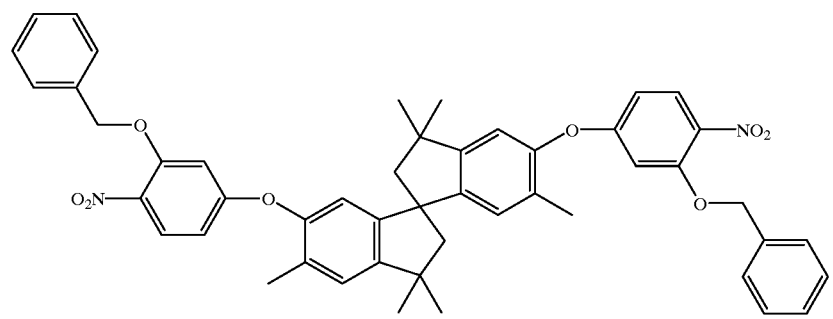

10.0 g of 6,6'-dihydroxy-5,5'-dimethyl-3,3,3',3'-tetramethyl-1,1'-spiro-bis(indane) (0.0297 mol) and 15.42 g of 3-fluoro-6-nitrobenzyloxybenzene (0.0624 mol) are dissolved in 50 ml of dimethylformamide. 10.26 g of $K_2CO_3$ (0.0743 mol) is then added and the mixture stirred continuously for 3 hours at 130° C. At the end of the reaction the mixture is cooled to room temperature and poured with stirring into 200 ml of water. The precipitated solid is filtered off using a Büchner funnel, washed once with dilute acetic acid and once with water and then dried in a vacuum chamber under nitrogen at 50° C./50 mbar.

The crude product is purified by recrystallization according to Example 1 with 100 ml of tetrahydrofuran and 100 ml of petroleum ether. Yield: 21.60 g Charcterization Mass spectrum: molecular ion at 790

Elemental analysis:

|  | C | H | N |
|---|---|---|---|
| Required (%): | 74.4 | 5.9 | 3.5 |
| Found (%): | 74.4 | 5.9 | 3.4 |

EXAMPLE 12

Preparation of 6,6'-bis[(4-amino-3-hydroxy)phenoxy]-5,5'-dimethyl-3,3,3',3'-tetramethyl-1,1'-spiro-bis(indane)

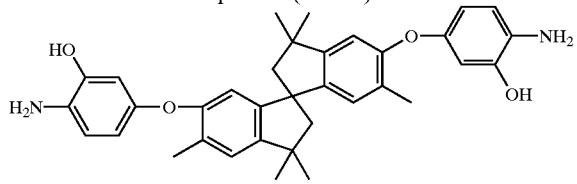

15.0 g of 6,6'-bis[(3-benzyloxy-4-nitro)phenoxy]-5,5'-dimethyl-3,3,3',3'-tetramethyl-1,1'-spiro-bis(indane) (0.019 mol) prepared according to Example 11 is dissolved in 150 ml of tetrahydrofuran, 1.5 g of palladium on active charcoal is added to the solution and the suspension is hydrogenated at room temperature in an autoclave with hydrogen at a pressure of 2 bar; the reaction is complete after 24 hours. The suspension is then filtered through a Büchner funnel and the orange colored filtrate is evaporated to dryness in a rotary evaporator.

For purification the crude product is dissolved in 100 ml of tetrahydrofuran at the boiling point and 250 ml of petroleum ether (bp 60–80° C.) is added. For crystallization the solution is kept at 4° C. for 24 hours and the pale brownish solid filtered off using a Büchner funnel and dried in the vacuum cabinet under nitrogen at 50° C./50 mbar. Yield: 9.8 g.

Charcterization

Mass spectrum: molecular ion at 550

Elemental analysis:

|  | C | H | N |
|---|---|---|---|
| Required (%): | 76.3 | 7.0 | 5.1 |
| Found (%): | 76.4 | 7.1 | 5.1 |

EXAMPLE 13

Preparation of 6-[(3-benzyloxy-4-nitro) phenoxy]-6'-hydroxy-5,5'-dimethyl-3,3,3',3'-tetramethyl-1,1'-spiro-bis(indane)

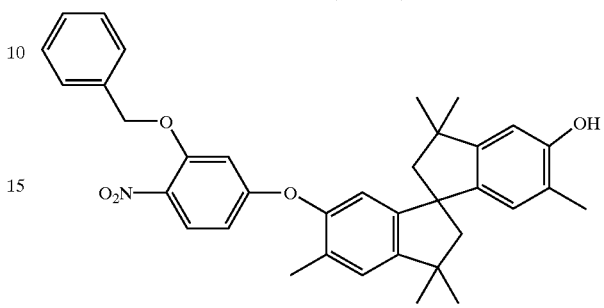

10.0 g of 6,6'-dihydroxy-5,5'-dimethyl-3,3,3',3'-tetramethyl-1,1'-spiro-bis(indane) (0.0297 mol) and 7.34 g of 3-fluoro-6-nitrobenzyloxybenzene(0.0297 mol) are dissolved in 50 ml of dimethylformamide. 10.26 g of $K_2CO_3$ (0.0743 mol) is then added and the mixture stirred continuously for 5 hours at 120° C. At the end of the reaction the mixture is cooled to room temperature and poured with stirring into 700 ml of water. The precipitated solid is filtered off using a Büchner funnel, washed once with dilute acetic acid and once with water and then dried in a vacuum chamber under nitrogen at 50° C./50 mbar.

The crude product is purified by recrystallization according to Example 1 with 80 ml of tetrahydrofuran and 80 ml of petroleum ether. Yield: 16.0 g Charcterization Mass spectrum: molecular ion at 563

Elemental analysis:

|  | C | H | N |
|---|---|---|---|
| Required (%): | 76.7 | 6.6 | 2.5 |
| Found (%): | 76.7 | 6.6 | 2.5 |

EXAMPLE 14

Preparation of 6-[(3-benzyloxy-4-nitro)phenoxy]-6'-[(4-benzylcarboxy)phenoxy]-5,5'-dimethyl-3,3,3',3'-tetramethyl-1,1'-spiro-bis(indane)

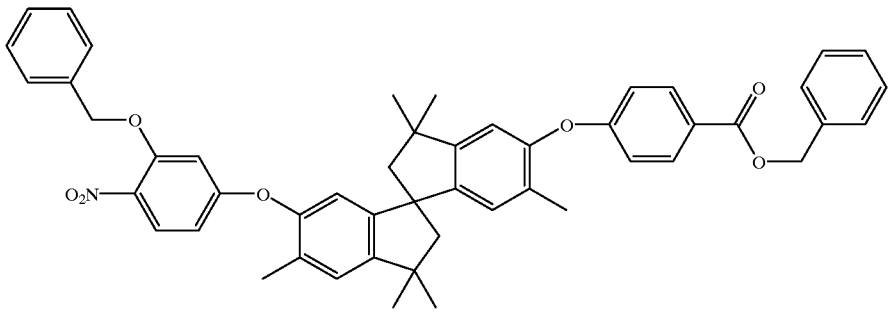

15.0 g of 6-[(3-benzyloxy-4-nitro)phenoxy]-6'-hydroxy-5,5'-dimethyl-3,3,3', 3'-tetramethyl-1,1'-spiro-bis(indane) (0.0266 mol) prepared according to Example 13 and 6.13 g of 4-fluorobenzoic acid benzyl ester (0.0266 mol) are are dissolved in 75 ml of dimethylformamide. 4.95 g of $K_2CO_3$ (0.0385 mol) is then added and the mixture stirred continuously for 5 hours at 130° C. At the end of the reaction the mixture is cooled to room temperature and poured with stirring into 400 ml of water. The precipitated solid is filtered off using a Büchner funnel, washed once with dilute acetic acid and once with water and then dried in a vacuum chamber under nitrogen at 50° C./50 mbar.

The crude product is purified by recrystallization according to Example 1 with 100 ml of tetrahydrofuran and 100 ml of petroleum ether. Yield: 18.5 g Charcterization Mass spectrum: molecular ion at 773

Elemental analysis:

|  | C | H | N |
|---|---|---|---|
| Required (%): | 77.6 | 6.1 | 1.8 |
| Found (%): | 77.6 | 6.0 | 1.9 |

EXAMPLE 15

Preparation of 6-[(4-amino-3-hydroxy)phenoxy]-6'-[(4-carboxy)phenoxy]-5,5'-dimethyl-3,3,3', 3'-tetramethyl-1,1'-spiro-bis(indane)

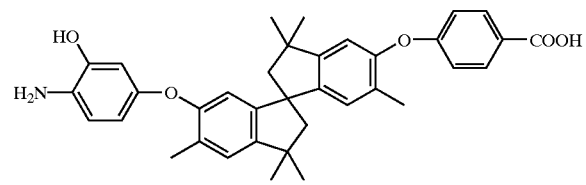

15.0 g of 6-[(3-benzyloxy-4-nitro)phenoxy]-6'-[(4-benzylcarboxy)phenoxy]-5,5'-dimethyl-3,3,3',3'-tetramethyl-1,1'-spiro-bis(indane) (0.019 mol) prepared according to Example 14 is dissolved in 200 ml of tetrahydrofuran, 1.5 g of palladium on active charcoal is added to the solution and the suspension is hydrogenated at room temperature in an autoclave with hydrogen at a pressure of 2 bar; the reaction is complete after 24 hours. The suspension is then filtered through a Büchner funnel and the filtrate is evaporated to dryness in a rotary evaporator.

The crude product is purified by recrystallization according to Example 2 with 150 ml of tetrahydrofuran and 50 ml of petroleum ether. Yield: 10.5 g Charcterization Mass spectrum: molecular ion at 563

Elemental analysis:

|  | C | H | N |
|---|---|---|---|
| Required (%): | 76.7 | 6.6 | 2.5 |
| Found (%): | 76.5 | 6.7 | 2.5 |

EXAMPLE 16

Preparation of 9,10-bis(4-[(3-benzyloxy-4-nitro)phenoxy]phenyl)anthracene

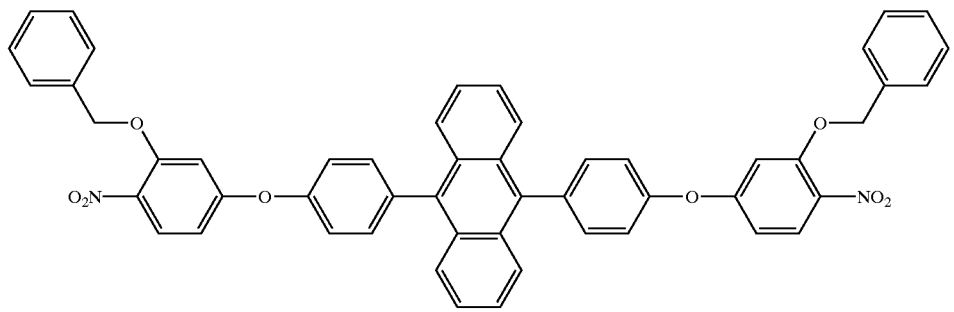

10.0 g of 9,10-bis(4-hydroxyphenyl)anthracene (0.0276 mol) and 14.0 g of 3-fluoro-6-nitrobenzyloxybenzene (0.0566 mol) are dissolved in 300 ml of dimethyl sulfoxide. 9.53 g of $K_2CO_3$ (0.069 mol) is then added and the mixture is stirred for 5 hours at 130° C. At the end of the reaction the mixture is cooled to room temperature and poured with stirring into 600 ml of water. The precipitated solid is filtered off using a Büchner funnel, washed once with dilute acetic acid and once with water and and then dried in a vacuum chamber under nitrogen at 50° C./50 mbar.

The crude product is purified by recrystallization according to Example 1 with 100 ml of tetrahydrofuran and 100 ml of petroleum ether. Yield: 21.73 g Charcterization Mass spectrum: molecular ion at 816

Elemental analysis:

|  | C | H | N |
|---|---|---|---|
| Required (%): | 76.5 | 4.4 | 3.4 |
| Found (%): | 76.4 | 4.4 | 3.4 |

EXAMPLE 17

Preparation of 9,10-bis(4-[(4-amino-3-hydroxy)phenoxy]phenyl)anthracene 10.0 g of 9,10-bis(4-[(3-benzyloxy-4-nitro)phenoxy]phenyl)anthracene (0.012 mol) prepared according to Example 16 is dissolved in 400 ml of a mixture of tetrahydrofuran and ethyl acetate (1:1 by volume), 1.0 g of palladium on active charcoal is added to the solution and the suspension is hydrogenated at room temperature in an autoclave with hydrogen at a pressure of 2 bar; the reaction is complete after 24 hours. The suspension is then filtered through a Büchner funnel and the filtrate is evaporated to dryness in a rotary evaporator.

The crude product is purified by recrystallization according to Example 2 with 100 ml of tetrahydrofuran and 30 ml of petroleum ether. Yield: 6.17 g Charcterization Mass spectrum: molecular ion at 576

Elemental analysis:

|  | C | H | N |
|---|---|---|---|
| Required (%): | 79.1 | 4.9 | 4.9 |
| Found (%): | 79.1 | 5.0 | 5.0 |

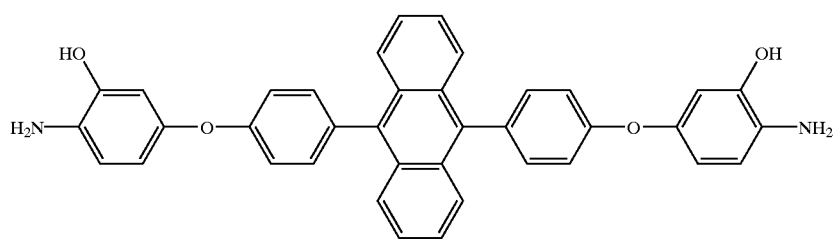

EXAMPLE 18

Preparation of 9-(4-[(3-benzyloxy-4-nitro)phenoxy]phenyl)-10-(4-hydroxyphenyl)anthracene

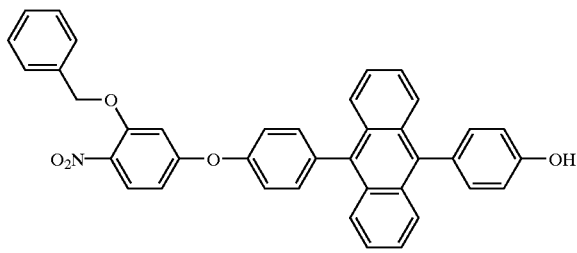

10.0 g of 9,10-bis(4-hydroxyphenyl)anthracene (0.0276 mol) and 6.82 g of 3-fluoro-6-nitrobenzyloxybenzene (0.0276 mol) are dissolved in 300 ml of dimethyl sulfoxide. 9.53 g of $K_2CO_3$ (0.069 mol) is then added and the mixture is stirred for 12 hours at 115° C. At the end of the reaction the mixture is cooled to room temperature and poured with stirring into 600 ml of water. The precipitated solid is filtered off using a Büchner funnel, washed once with dilute acetic acid and once with water and then dried in a vacuum chamber under nitrogen at 50° C./50 mbar.

The crude product is purified by recrystallization according to Example 1 with 100 ml of tetrahydrofuran and 100 ml of petroleum ether. Yield: 15.80 g Charcterization Mass spectrum: molecular ion at 589

Elemental analysis:

|  | C | H | N |
|---|---|---|---|
| Required (%): | 79.4 | 4.6 | 2.4 |
| Found (%): | 79.4 | 4.6 | 2.4 |

EXAMPLE 19

Preparation of 9-(4-[(3-benzyloxy-4-nitro)phenoxy]phenyl)-10-(4-[(4-benzylcarboxy)phenoxy]phenyl)anthracene 15.0 g of 9-(4-[(3-benzyloxy-4-nitro)phenoxy]phenyl)-10-(4-hydroxyphenyl)anthracene (0.0254 mol) and 6.82 g of 4-fluorobenzoic acid benzyl ester (0.0296 mol) are dissolved in 300 ml of dimethyl sulfoxide. 4.49 g of $K_2CO_3$ (0.0325 mol) is then added and the mixture is stirred for 2 hours at 140° C. At the end of the reaction the mixture is cooled to room temperature and poured with stirring into 600 ml of water. The precipitated solid is filtered off using a Büchner funnel, washed once with dilute acetic acid and once with water and and then dried in a vacuum chamber under nitrogen at 50° C./50 mbar.

The crude product is purified by recrystallization according to Example 1 with 100 ml of tetrahydrofuran and 100 ml of petroleum ether. Yield: 17.76 g Charcterization Mass spectrum: molecular ion at 799

Elemental analysis:

|  | C | H | N |
|---|---|---|---|
| Required (%): | 79.6 | 4.7 | 1.8 |
| Found (%): | 79.4 | 4.6 | 1.7 |

EXAMPLE 20

Preparation of 9-(4-[(4-amino-3-hydroxy)phenoxy]phenyl)-10-(4-[(4-carboxy)phenoxy]phenyl)anthracene

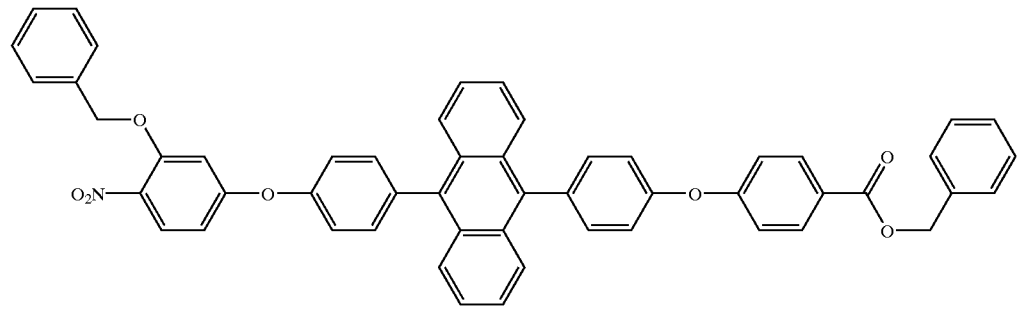

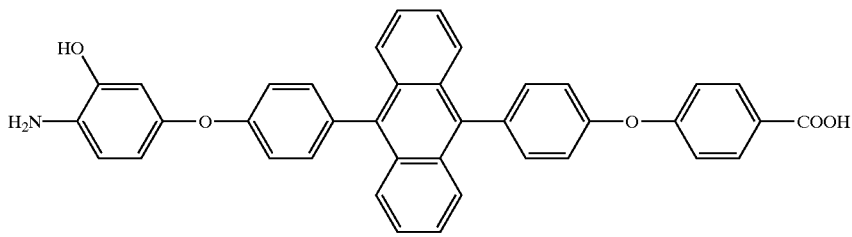

15.0 g of 9-(4-[(3-benzyloxy-4-nitro)phenoxy]phenyl)-10-(4-[(4-benzylcarboxy)phenoxy]phenyl)anthracene (0.0188 mol) prepared according to Example 19 is dissolved in 600 ml of a mixture of tetrahydrofuran and ethyl acetate (1:1 by volume), 1.5 g of palladium on active charcoal is added to the solution and the suspension is hydrogenated at room temperature in an autoclave with hydrogen at a pressure of 2 bar; the reaction is complete after 24 hours. The suspension is then filtered through a Büchner funnel and the filtrate is evaporated to dryness in a rotary evaporator.

The crude product is purified by recrystallization according to Example 2 with 100 ml of tetrahydrofuran and 30 ml of petroleum ether. Yield: 10.91 g Charcterization Mass spectrum: molecular ion at 589

Elemental analysis:

|  | C | H | N |
|---|---|---|---|
| Required (%): | 79.4 | 4.6 | 2.4 |
| Found (%): | 79.4 | 4.6 | 2.4 |

We claim:

1. Bis-o-aminophenols and o-aminophenolcarboxylic acids represented by respective structures:

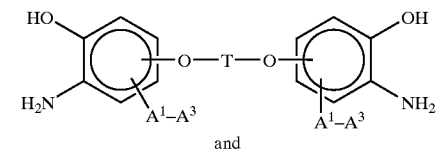

and

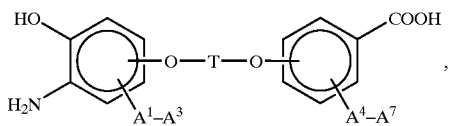

wherein each of $A^1$ to $A^7$ is a univalent ring substituent independently selected from the group consisting of H, F, $CH_3$, $CF_3$, $OCH_3$ and $OCF_3$;

T is a bivalent polycyclic linking member selected from the group consisting of:

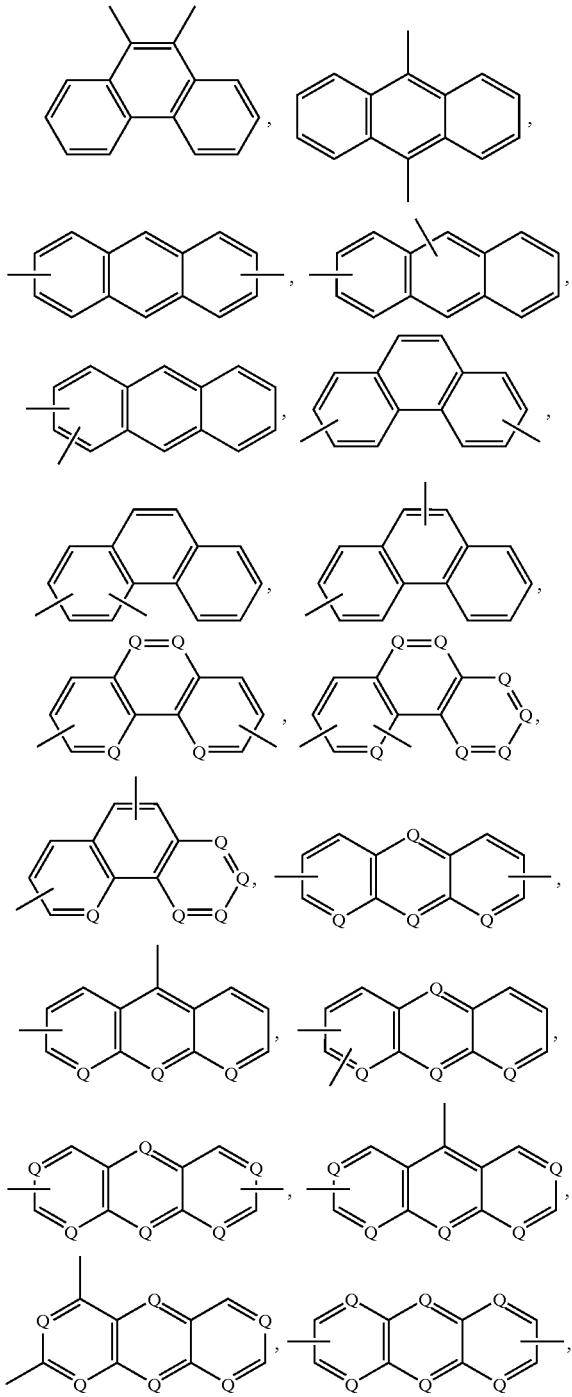

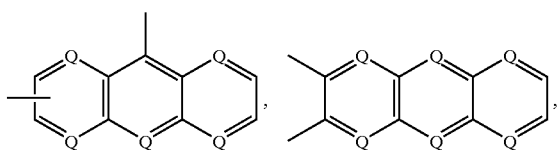

wherein independently at each occurrence Q is selected from the group consisting of C—H, C—F, C—CH$_3$, C—CF$_3$, C—OCH$_3$, C—OCF$_3$ or N, provided that at least one Q signifies N and a maximum of two N atoms may be present in a single ring

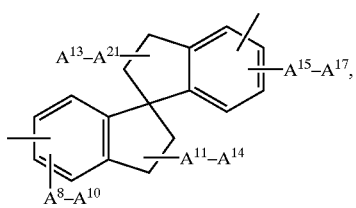

wherein each of $A^8$ to $A^{21}$ is a univalent ring substituent independently selected from the group consisting of H, F, CH$_3$, CF$_3$, OCH$_3$ and OCF$_3$;

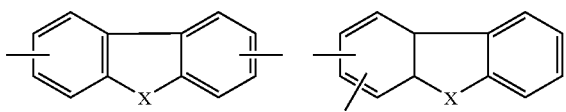

wherein X signifies CH$_2$, CF$_2$, C(CH$_3$)$_2$, C(CF$_3$)$_2$, C(OCH$_3$)$_2$, C(OCF$_3$)$_2$, C(CH$_3$) (C$_6$H$_5$), C(C$_6$H$_5$)$_2$, O, N—H, N—CH$_3$ or N—C$_6$H$_5$;

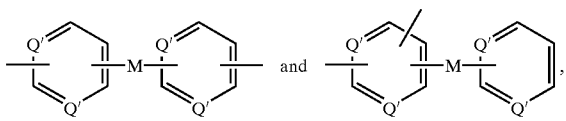 and wherein
independently at each occurrence Q' is selected from the group consisting of C—H, C—F, C—CH$_3$, C—CF$_3$, C—OCH$_3$, C—OCF$_3$ or N,
and M is a bivalent linking member selected from the group consisting of

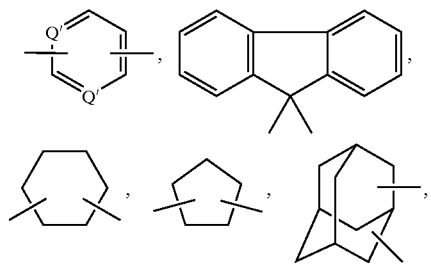

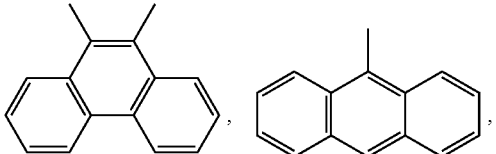

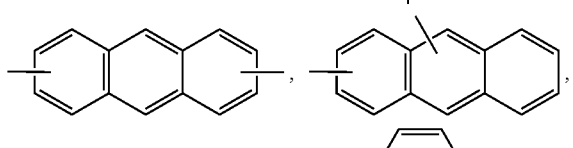

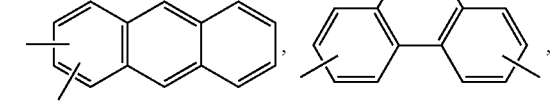

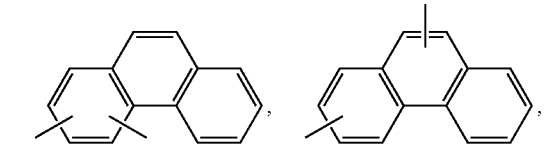

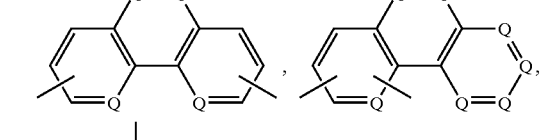

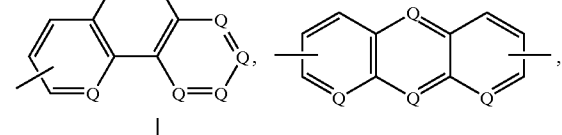

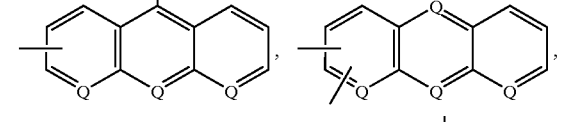

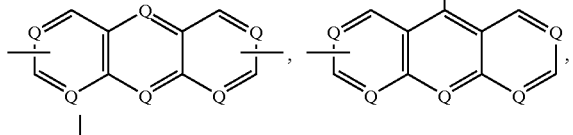

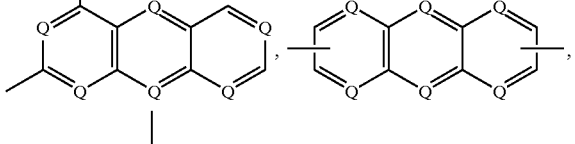

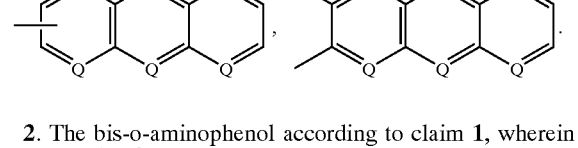

2. The bis-o-aminophenol according to claim 1, wherein each of $A^1$–$A^3$ is H.

3. The o-aminophenolcarboxylic acid according to claim 1, wherein each of $A^1$–$A^7$ is H.

4. The o-aminophenolcarboxylic acid according to claim 1, wherein at least one of $A^4$–$A^7$ is CF$_3$.

5. The bis-o-aminophenols and o-aminophenolcarboxylic acids according to claim 1, wherein T is

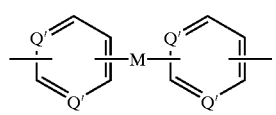

each Q' is C—H, and M is

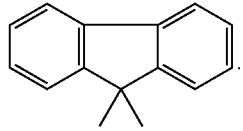

6. The bis-o-aminophenols and o-aminophenolcarboxylic acids according to claim 1, wherein T is

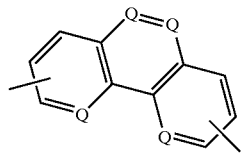

and Q is N in the left hand and right hand rings and C—H at each occurrence in the middle ring.

7. The bis-o-aminophenols and o-aminophenolcarboxylic acids according to claim 1, wherein T is

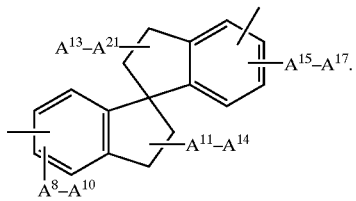

8. The bis-o-aminophenols and o-aminophenolcarboxylic acids according to claim 1, wherein T is

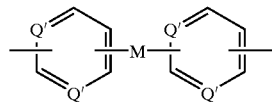

each Q' is C—H, and M is

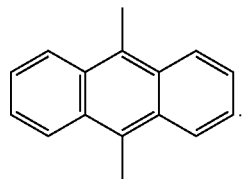

9. The bis(o-aminophenol) according to claim 1, represented by the formula:

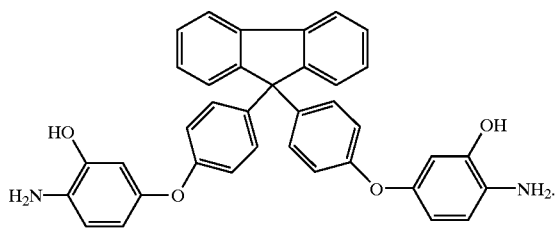

10. The bis(o-aminophenol) according to claim 1, represented by the formula:

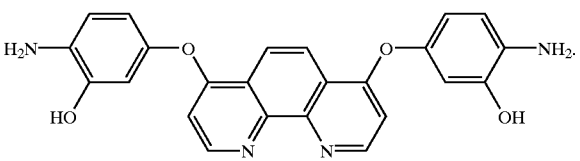

11. The bis(o-aminophenol) according to claim 1, represented by the formula:

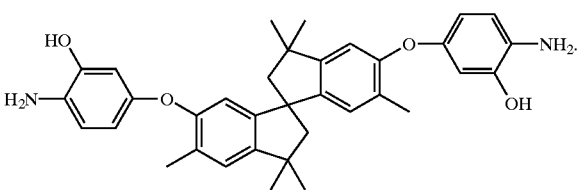

12. The bis(o-aminophenol) according to claim 1, represented by the formula:

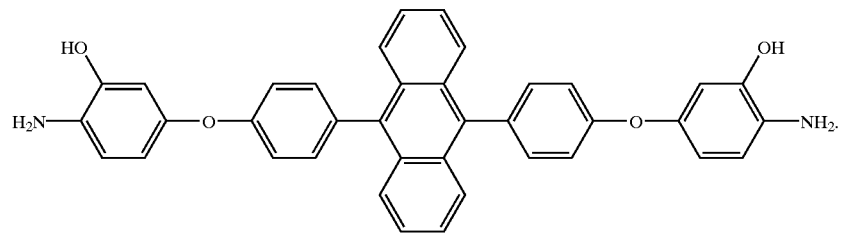

13. The o-aminophenolcarboxylic acid according to claim 1, represented by the formula:

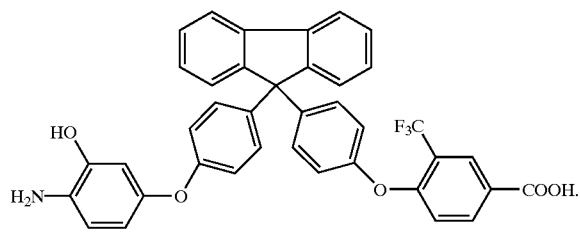

14. The o-aminophenolcarboxylic acid according to claim 1, represented by the formula:

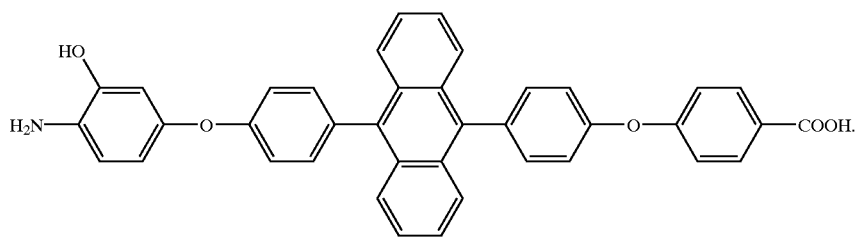

15. The o-aminophenolcarboxylic acid according to claim 1, represented by the formula:

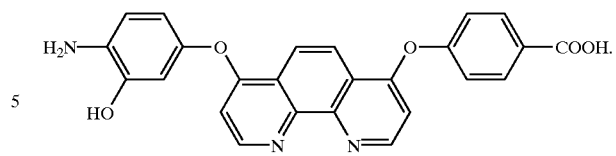

15. The o-aminophenolcarboxylic acid according to claim 1, represented by the formula:

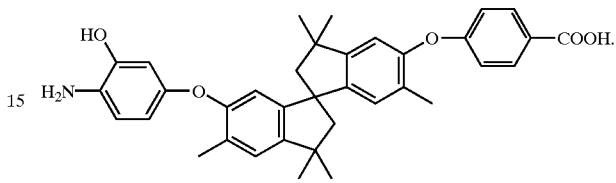

16. The o-aminophenolcarboxylic acid according to claim 1, represented by the formula:

* * * * *